(12) United States Patent
Meyer et al.

(10) Patent No.: US 7,968,616 B2
(45) Date of Patent: Jun. 28, 2011

(54) BONE CEMENT COMPOSITION AND METHOD

(75) Inventors: Jörg Meyer, Heusenstramm (DE); Robert Wenz, Wöllstadt (DE)

(73) Assignee: Kyphon Sarl, Neuchatel (CH)

( * ) Notice: Subject to any disclaimer, the term of this patent is extended or adjusted under 35 U.S.C. 154(b) by 191 days.

(21) Appl. No.: 12/107,273

(22) Filed: Apr. 22, 2008

(65) Prior Publication Data

US 2009/0264554 A1 Oct. 22, 2009

(51) Int. Cl.
*A61B 17/58* (2006.01)
(52) U.S. Cl. .......................................... 523/117; 606/94
(58) Field of Classification Search .................. 523/117; 606/94
See application file for complete search history.

(56) References Cited

U.S. PATENT DOCUMENTS

| | | | |
|---|---|---|---|
| 3,746,680 A | 7/1973 | Boricheski |
| 4,141,864 A | 2/1979 | Rijke et al. |
| 4,192,021 A | 3/1980 | Deibig et al. |
| 4,239,113 A | 12/1980 | Gross et al. |
| 4,341,691 A | 7/1982 | Anuta |
| 4,404,327 A | 9/1983 | Crugnola |
| 4,518,430 A | 5/1985 | Brown et al. |
| 4,588,583 A | 5/1986 | Pietsch et al. |
| 4,612,053 A | 9/1986 | Brown et al. |
| 4,629,464 A | 12/1986 | Takata et al. |
| 4,678,436 A | 7/1987 | Kondo et al. |
| 4,722,948 A | 2/1988 | Sanderson |
| 4,791,150 A | 12/1988 | Braden et al. |
| 4,872,936 A | 10/1989 | Engelbrecht |
| 4,902,649 A | 2/1990 | Kimura et al. |
| 4,940,689 A | 7/1990 | Ito |
| 4,957,352 A | 9/1990 | Yasuda et al. |
| 4,959,104 A | 9/1990 | Iino et al. |
| 5,004,501 A | 4/1991 | Faccioli |
| 5,108,956 A | 4/1992 | Inoue et al. |
| 5,149,368 A | 9/1992 | Liu et al. |
| 5,160,371 A | 11/1992 | Ito |
| 5,171,720 A | 12/1992 | Kawakami |
| 5,179,065 A | 1/1993 | Ito |
| 5,204,382 A | 4/1993 | Wallace et al. |
| 5,205,928 A | 4/1993 | Inoue et al. |
| 5,226,877 A | 7/1993 | Epstein |
| 5,262,166 A | 11/1993 | Liu et al. |
| 5,276,070 A | 1/1994 | Arroyo |
| 5,281,265 A | 1/1994 | Liu |
| 5,352,715 A | 10/1994 | Wallace et al. |
| 5,462,356 A | 10/1995 | Murray |
| 5,462,722 A | 10/1995 | Liu et al. |
| 5,522,893 A | 6/1996 | Chow et al. |
| 5,545,254 A | 8/1996 | Chow et al. |
| 5,605,713 A | 2/1997 | Boltong |
| 5,650,108 A | 7/1997 | Nies et al. |
| 5,695,729 A | 12/1997 | Chow et al. |
| 5,795,922 A | 8/1998 | Demian et al. |
| 5,797,873 A | 8/1998 | Franz et al. |
| 5,814,683 A | 9/1998 | Branham |
| 5,847,046 A | 12/1998 | Jiang et al. |
| 5,914,356 A | 6/1999 | Erbe |
| 5,952,010 A | 9/1999 | Constantz |
| 6,002,065 A | 12/1999 | Constantz et al. |
| 6,075,067 A | 6/2000 | Lidgren |
| 6,124,373 A | 9/2000 | Peter et al. |
| 6,153,664 A | 11/2000 | Wise et al. |
| 6,187,046 B1 | 2/2001 | Yamamoto et al. |
| 6,203,574 B1 | 3/2001 | Kawamura |
| 6,206,957 B1 | 3/2001 | Driessens et al. |
| 6,224,635 B1 | 5/2001 | Ricci et al. |
| 6,231,615 B1 | 5/2001 | Preissman |
| 6,241,734 B1 | 6/2001 | Scribner et al. |
| 6,248,110 B1 | 6/2001 | Reiley et al. |
| 6,273,916 B1 | 8/2001 | Murphy |
| 6,309,420 B1 | 10/2001 | Preissman |
| 6,325,992 B1 | 12/2001 | Chow et al. |
| 6,338,810 B1 | 1/2002 | Carpena et al. |
| 6,436,143 B1 | 8/2002 | Ross et al. |
| 6,497,901 B1 | 12/2002 | Royer |
| 6,521,264 B1 | 2/2003 | Lacout et al. |
| 6,547,866 B1 | 4/2003 | Edwards et al. |
| 6,562,755 B1 | 5/2003 | Halbrook, Jr. et al. |
| 6,593,394 B1 | 7/2003 | Li et al. |
| 6,613,054 B2 | 9/2003 | Scribner et al. |
| 6,692,563 B2 | 2/2004 | Zimmermann |
| 6,908,506 B2 | 6/2005 | Zimmermann |
| 6,953,594 B2 | 10/2005 | Lee et al. |

(Continued)

FOREIGN PATENT DOCUMENTS

DE 29607832 10/1996

(Continued)

OTHER PUBLICATIONS

Abdullah et al., Biodegradable Polymeric Bone Cement Formed from Hydroxyapatite, Poly (Propylene Fumerate), Poly (Vinyl Pyrolidone) and Benzoyl Peroxide, Materials Science and Technology, vol. 20, No. 9, pp. 1084-1086 (2004) (abstract only). Baroud et al., Influence of Oscillatory Mixing on the Injectability of Three Acrylic and Two Calcium-Phosphate Bone Cements for Vertebroplasty, J Biomed Mater Res, vol. 68B, No. 1, pp. 105-111 (2004) (abstract only).
Beruto et al., Use of Alpha-Tricalcium Phosphate (TCP) as Powders and as an Aqueous Dispersion to Modify Processing, Microstructure, and Mechanical Properties of Polymethylmethacrylate (PMMA) Bone Cements and to Produce Bone-Substitute Compounds, J Biomed Mater Res, vol. 49, No. 4, pp. 498-505 (2000) (abstract only).
Bezzi G. et al., A novel sol-gel technique for hydroxyapatite preparation, Materials Chemistry and Physics, 2003, 78: 816-824, entire document.
Bonfield et al., Hydroxyapatite Composite Biomaterials—Evolution and Applications, Materials World, vol. 5, No. 1, pp. 18-20 (1997).
Brown, et al., A new calcium phosphate, water-setting cement, Cements Research Progress 1986 pp. 352-379 (1987).
Canul-Chuil et al., Comparative Study of Bone Cements prepared with either HA or alpha-TCP and Functionalized Methacrylates, J Biomed Mater Res, vol. 64B. No. 1, pp. 27-37 (2003) (abstract only).

(Continued)

Primary Examiner — Robert D. Harlan

(57) ABSTRACT

The disclosure is directed to a composition includes a first component and a second component. The first component includes a poly(methyl methacrylate) (PMMA), a contrast agent, and a radical donor. The second component includes methyl methacrylate (MMA), a radical scavenger, and a polymerization accelerator. The composition has an average setting time of about 13 minutes. The disclosure is further directed to a kit and a method of making the above-mentioned composition.

16 Claims, 1 Drawing Sheet

U.S. PATENT DOCUMENTS

| | | |
|---|---|---|
| 6,994,726 B2 | 2/2006 | Lin et al. |
| 7,008,433 B2 | 3/2006 | Voellmicke |
| 7,115,163 B2 | 10/2006 | Zimmermann |
| 7,135,027 B2 | 11/2006 | Delmotte |
| 7,138,442 B2 | 11/2006 | Smith |
| 7,160,932 B2 | 1/2007 | Schilke |
| 7,273,523 B2 | 9/2007 | Wenz |
| 2001/0012968 A1 | 8/2001 | Preissman |
| 2002/0152929 A1 | 10/2002 | Burgath et al. |
| 2002/0167480 A1 | 11/2002 | Johnson et al. |
| 2002/0187104 A1 | 12/2002 | Li et al. |
| 2002/0191487 A1 | 12/2002 | Sand |
| 2003/0031698 A1 | 2/2003 | Roeder et al. |
| 2003/0032964 A1 | 2/2003 | Watkins |
| 2003/0055512 A1 | 3/2003 | Genin et al. |
| 2003/0139488 A1 | 7/2003 | Wojciak |
| 2003/0161858 A1 | 8/2003 | Lidgren |
| 2003/0180344 A1 | 9/2003 | Wise et al. |
| 2004/0048947 A1 | 3/2004 | Lidgren et al. |
| 2004/0122359 A1 | 6/2004 | Wenz et al. |
| 2004/0157952 A1 | 8/2004 | Soffiati et al. |
| 2004/0226479 A1 | 11/2004 | Lyles et al. |
| 2004/0265385 A1 | 12/2004 | West |
| 2005/0105384 A1 | 5/2005 | Eder et al. |
| 2005/0142211 A1 | 6/2005 | Wenz |
| 2005/0199156 A1 | 9/2005 | Khairoun et al. |
| 2005/0246036 A1 | 11/2005 | Zimmermann |
| 2005/0256220 A1 | 11/2005 | Lavergne |
| 2006/0079905 A1 | 4/2006 | Beyar |
| 2007/0021526 A1 | 1/2007 | He et al. |
| 2007/0027230 A1* | 2/2007 | Beyar et al. .................. 523/117 |
| 2007/0032567 A1 | 2/2007 | Beyar |
| 2007/0048382 A1 | 3/2007 | Meyer et al. |
| 2007/0128245 A1 | 6/2007 | Rosenberg et al. |
| 2007/0191964 A1 | 8/2007 | Preissman |
| 2007/0254011 A1 | 11/2007 | Schnabelrauch et al. |

FOREIGN PATENT DOCUMENTS

| | | |
|---|---|---|
| DE | 20218668 | 3/2003 |
| DE | 20218668 U1 | 3/2003 |
| EP | 0473048 A2 | 3/1992 |
| EP | 0511868 A2 | 11/1992 |
| EP | 0520690 A2 | 12/1992 |
| EP | 0543765 A1 | 5/1993 |
| EP | 1002513 A1 | 5/2000 |
| EP | 1255576 B1 | 8/2003 |
| EP | 0835668 B1 | 11/2007 |
| JP | 01320251 | 12/1989 |
| JP | 02116684 | 5/1990 |
| WO | WO9202478 A1 | 2/1992 |
| WO | WO9513835 A1 | 5/1995 |
| WO | WO9614265 A1 | 5/1996 |
| WO | WO0149327 A2 | 7/2001 |
| WO | WO0232827 A1 | 4/2002 |
| WO | WO0236518 A1 | 5/2002 |
| WO | WO03086327 A2 | 10/2003 |
| WO | WO03103734 A1 | 12/2003 |
| WO | WO2004050131 A1 | 6/2004 |
| WO | 2005009481 A2 | 2/2005 |
| WO | WO2007025633 A2 | 3/2007 |
| WO | WO2007067561 A2 | 6/2007 |

OTHER PUBLICATIONS

Chu et al., Hydroxyapatite/PMMA Composites as Bone Cements, Biomed Mater Eng, vol. 14, No. 1, pp. 87-105 (2004) (abstract only).

Dalby et al., Initial Interaction of Osteoblasts with the Surface of a Hydroxyapatite-Poly (Methylmethacrylate) Cement, Biomaterials, vol. 22, No. 13, pp. 1739-1747 (2001) (abstract only).

Eule et al., Bioactive Bone Cement: The Solution for Osteolysis and Late Implant Loosening, SRS Annual Meeting: Scientific Program Abstracts, pp. 98 (2002).

Frankenburg et al., Evaluation of Hydroxyapatite/Bis-GMA Bone Cement for Fixation of Cemented Hip Stems, The Third Combined Meeting of the Orthopaedic Research Societies of the USA, Canada, Europe and Japan, Hamamatsu City, Japan (1998).

Grigorian et al., Evolution of Tissue Structures in the Mandible after Implantation of Plate from Polymethylmethacrylate and its Compositions with Hydroxyapatite, Stomatolgiia, vol. 82, No. 2, pp. 10-14 (2003) (abstract only).

Harper et al., Tensile Characteristics of Ten Commerical Acrylic Bone Cements, J Biomed Mater Res:Appl Biomater., vol. 53, pp. 605-616 (2000) (abstract only).

Heness et al., Biocomposites—Bone Cement, Hydroxyapatite and Biomimetic Composites for Bone Repair, Innovative Bioceramics, Materials Forum, vol. 27 (2004) (3 page abstract).

Hitchon et al., Comparison of the Biomechanics of Hydroxyapatite and Polymethylmethacrylate Vertebroplasty in a Cadaveric Spinal Compression Fracture Model, J. Neurosurg, vol. 95, Suppl. 2, pp. 215-220, (2001) (abstract only).

Ishikawa et al., Effects of neutral sodium hydrogen phosphate on setting reaction and mechanical strength of hydroxyapatite putty, J Biomed Mater Res, 44, 322-329, 1999.

Ishikawa et al., Non-decay type fast-setting calcium phosphate cement Hydroxyapatite putty containing an increased amount of sodium alginate, J Biomed Mater Res, 36, 393-399, 1997.

Jager et al., Comprehensive Biocompatibility Testing of a New PMMA-hA Bone Cement Versus Conventional PMMA Cement in Vitro, J. Biomater Sci Polym Ed, vol. 14, No. 11, pp. 1283-1298 (2003). (abstract only).

Lee C L et al., Laser Ablation of Dyed Acrylic Bone Cement, Lasers in Surgery and Medicine, Wiley-Liss, New York, US vol. 20, 3, Jan. 1, 1997, pp. 280-289, XP000694435, ISSN:0196-8092.

Lee R.R. et al, Interactions between bone and hydroxyapatite filled 4 META/MMA-TBB adhesive cement in vitro and in physiological environment, 1996, IEEE Xplore, pp. 18-21, entire document.

Li et al., A Novel Injectable Bioactive Bone Cement for Spinal Surgery: A Developmental and Preclinical Study, J Biomed Mater Res, vol. 52, No. 1,,pp. 164-170 (2000) (abstract only).

Liu et al., Influence of the Aspect Ratio of Bioactive Nanofillers on Rheological Behavior of PMMA-Based Orthopedic Materials, J Biomed Mater Res, vol. 71B, No. 1, pp. 116-122 (2004) (abstract only).

Liao et al., A Fundamental Study on Bioreactions of Sr-HA, Hua Xi Kou Qiang Yi Xue Za Zhi, vol. 20, No. 3, pp. 172-174 183 (2002) (abstract only).

Miyazaki et al., Bioactive PMMA Bone Cement Prepared by Modification with Methacryloxypropyltrimethoxysilane and Calcium Chloride, J Biomed Mater Res, vol. 67A, No. 4, pp. 1417-1423 (2003) (abstract only).

Mousa et al., Biological and Mechanical Properties of PMMA-Based Bioactive Bone Cements, Biomaterials, vol. 21, No. 21, pp. 2137-2146 (2000) (abstract only).

Okada et al., Transmission Electron Microscopic Study of Interface Between Bioactive Bone Cement and Bone: Comparison of Apatite and Wollastonite Containing Glass-Ceramic Filler with Hydroxyapatite and Beta-Tricalcium Phosphate Filler, J Biomed Mater Res, vol. 45, No. 4, pp. 277-284 (1999) (abstract only).

Oonishi et al., Hydroxyapatite Granules Interposed at Bone-Cement Interface in Total Hip Replacements: Histological Study of Retrieved Specimens, J Biomed Mater Res, vol. 53, No. 2, pp. 174-180 (2000) (abstract only).

Patel et al., Comparison of Sintering and Mechanical Properties of Hydroxyapatite and Silicon-Substituted Hydroxyapatite, Key Engineering Materials, 240-242, 919-22 (2003) (abstract only).

Patent Abstract XP-002180738 (1 page total), Park et al., "Compositional effects of CaO-SiO2-P205 bioactive cement on hardening and hydroxyapatite formation" Yoop Hakhoechi, 31(5):502-512 (1994).

Patent Abstract XP-002180739 (1 page total), Nippon Electric Glass Co., "Bone-repair material for fast, strong bonding—contains glass and/or crystalline glass powder, a.q. phosphate solution and bond formation promoter" (1992).

The term "PRE-", Merriam-Webster Online Dictionary, at the web: http://www.m-w.com , p. 1-2. (Sep. 17, 2006).

Serbetci et al., Mechanical and Thermal Properties of Hydroxyapatite-Impregnated Bone Cement, Turk J Med Sci, vol. 30, pp. 543-549 (2000) (abstract only).

Turner et al., Hydroxyapatite Composite Resin Cement Augmentation of Pedicle Screw Fixation, Clinical Orthopaedics & Related Research, vol. 1, No. 406, pp. 253-261 (2003) (abstract only).

Wong et al., In Vivo Cancellous Bone Remodeling on a Strontium-Containing Hydroxyapatite (sr-HA) Bioactive Cement, J Biomed Mater Res A, vol. 68, No. 3, pp. 513-521 (2004) (abstract only).).

Wong et al., Ultrastructural Study of Mineralization of a Strontium-Containing Hydroxyapatite (Sr-HA) Cement in Vivo, J Biomed Mater Res A, vol. 70, No. 3, pp. 428-435 (2004) (abstract only.

Zhao et al., Surface Treatment of Injectable Strontium-Containing Bioactive Bone Cement for Vertebroplasty, J. Biomed Mater Res B Appl Biomater, vol. 69, No. 1, pp. 79-86 (2004) (abstract only).

International Search Report, WIPO, Jan. 22, 2009.

International Search Report and Written Opinion, International Application No. PCT/US2007/012723, mailed Dec. 3, 2008.

International Search Report and Written Opinion, International Application No. PCT/US2007/008789, mailed Nov. 13, 2008.

International Search Report and Written Opinion, International Application No. PCT/EP2006/007750, mailed Jun. 11, 2007.

International Search Report, International Application No. PCT/US03/38580, mailed May 19, 2004.

International Search Report, International Application No. PCT/US2005/014616, mailed Sep. 12, 2005.

Heini, P.F., et al., "Bone substitutes in vertebroplasty," *Eur. Spine J.*, Jun. 14, 2001, vol. 10, pp. S205-S213.

Li, Y., et al. "Preparation of amorphous calcium phosphate in the presence of poly(ethylene glycol)," *Journal of Materials Science Letters*, 2003, vol. 22, pp. 1015-1016.

* cited by examiner

BONE CEMENT COMPOSITION AND METHOD

FIELD OF THE DISCLOSURE

This disclosure, in general, relates to a bone cement composition, a kit and a method of making the bone cement composition.

BACKGROUND

Bone cement compositions are useful in applications such as dental and medical procedures. In particular, they are used in bonding or affixing an implant material to natural bone and to repair damaged natural bone. Although bone cement compositions enjoy wide use in the medical arts, these compositions need to be carefully designed depending on the surgical site at which they will be used. For example, compositions suitable for use in repairing a damaged bone in a limb may not be ideally suited for use in repairing damaged teeth. Similarly, compositions useful in repairing a limb or a tooth may not be ideally suited for surgically repairing the spinal column.

Typically, current bone cement compositions are sold in two-part preparations containing a powder (or dry) part and a liquid (or wet) part, which, when combined, polymerize to form a hardened substance mimicking many of the physical properties of natural bone. The powder part typically includes a polymeric material, such as acrylate polymers, while the liquid part includes a reactive monomer, such as methylmethacrylate. Recent developments have focused on modifying the bone cement composition for particular medical procedures.

For example, to attach prostheses to bone, Faccioli et al. (U.S. Pat. No. 5,004,501) discloses a bone cement composition having a polymer with submicron particle size, i.e. less than 0.9 microns. As stated in Faccioli et al., the function of the submicron particles is to fill any voids left in the bone cement composition to produce stronger bone cement. The patent further discloses the use of fluoride salts to produce a stronger bond between the bone cement and the bone of the patient.

For particular medical applications such as vertebroplasty, manufacturers have turned to producing bone cement compositions having radiopacity and longer setting times. For example, Layergne et al. (U.S. Patent Application No. 2005/0256220) describes a bone cement composition having setting times greater than 15 minutes. In particular, the bone cement is a polymethyl methacrylate (PMMA)-based composition. Layergne et al. achieves a longer setting time using a PMMA-based composition that includes hydroxyapatite and barium sulfate.

In another example of bone cements for vertebroplasty procedures, Voellmicke et al. (U.S. Pat. No. 7,008,433 and U.S. Patent Application No. 2003/0032964) describe a PMMA-based composition to provide radiopacity and further increase the setting time of the bone cement. Specifically, the bone cement composition has a setting time that is at least greater than 18 minutes. To produce a bone cement with a higher setting time and increased radiopacity, Voellmicke et al. use barium sulfate at amounts of 20% by weight to 40% by weight. The barium sulfate particles have $D_{50}$ sizes of greater than 3 microns and require 50% of the barium sulfate particles to be unbound (i.e. free) from the PMMA particles.

Other applications have focused on increasing the viscosity of the bone cement composition at an accelerated rate to infiltrate the medical site and prevent any migration of the cement during medical procedures. In particular, Beyar et al. (U.S. Patent Application Nos. 2007/0027230 and 2007/0032567), focus on a viscosity greater than 500 Pascal-second at 2 minutes after the initiation of mixing the two components of the bone cement composition. The U.S. patent applications of Beyar et al. achieve a high viscosity at an expedited rate by using one or more sub-population PMMA beads with a molecular weight that is significantly different than a main population of PMMA beads.

Bone cement compositions have been modified to have properties such as longer setting times and high viscosity produced at accelerated speeds. However, these properties are not beneficial for all medical application. Hence, it would be desirable to provide an improved bone cement composition.

SUMMARY

In a particular embodiment, a composition includes a first component and a second component. The first component includes a poly(methyl methacrylate) (PMMA), a contrast agent, and a radical donor. The second component includes methyl methacrylate (MMA), a radical scavenger, and a polymerization accelerator. The composition has an average setting time of about 13 minutes.

In another embodiment, a kit includes a packaged first component and a packaged second component. The packaged first component includes a poly(methyl methacrylate) (PMMA), a radical donor and a contrast agent. The second packaged component includes methyl methacrylate (MMA), a radical scavenger, and a polymerization accelerator. The mixed first component and second component have an average setting time of about 13 minutes.

In another exemplary embodiment, a method is provided. The method includes mixing a first component and a second component. The first component includes a poly(methyl methacrylate) (PMMA), a radical donor and a contrast agent. The second component includes methyl methacrylate (MMA), a radical scavenger, and a polymerization accelerator. The method further includes providing a set bone cement composition after an average time of about 13 minutes.

BRIEF DESCRIPTION OF THE DRAWINGS

The present disclosure may be better understood, and its numerous features and advantages made apparent to those skilled in the art by referencing the accompanying drawings.

DESCRIPTION OF THE DRAWINGS

Figure 1:
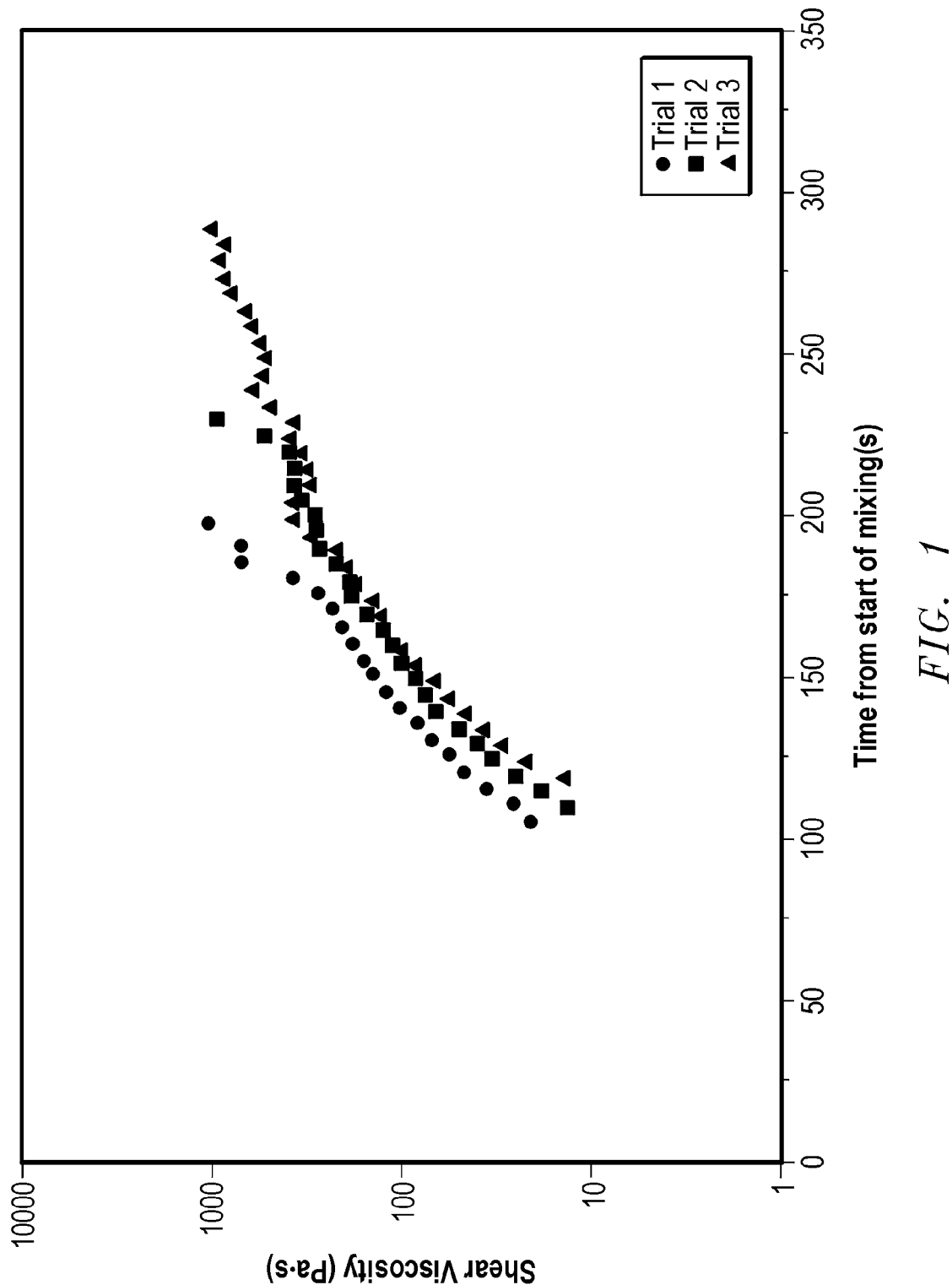
FIG. 1 includes graphical illustration of data representing the viscosity of exemplary bone cement compositions.

In a particular embodiment, a bone cement composition includes a first component and a second component. The first component includes a pre-polymerized vinyl polymer, a contrast agent, and a radical donor. The second component includes a reactive monomer, a radical scavenger, and a polymerization accelerator. The composition is a bone cement that has an average setting time of about 13 minutes. The bone cement composition is typically prepared by homogeneously mixing the first component with the second component using any suitable mixing method.

The first component of the bone cement composition is referred to as a dry or powder component. In an exemplary embodiment, the first component includes a pre-polymerized vinyl polymer. Pre-polymerized vinyl polymers include, for example, any medically suitable pre-polymerized polymers containing vinyl groups. Exemplary medically suitable pre-polymers include pre-polymerized acrylate polymers such as poly(methyl methacrylate) (PMMA), pre-polymerized styrene acrylates, poly-methacrylate, poly-ethacrylate, poly-butylmethacrylate, copolymers, and mixtures thereof. In an exemplary embodiment, the pre-polymerized vinyl polymer is poly(methyl methacrylate) (PMMA).

Typically, the pre-polymerized vinyl polymer has a molecular weight of about 200,000 grams/mole to about 500,000 grams/mole. In an embodiment, the pre-polymerized vinyl polymer has an average particle size up to about 100.0 microns. In an embodiment, the pre-polymerized vinyl polymer has an average particle size of about 1.0 micron to about 100.0 microns. In a particular embodiment, the pre-polymerized vinyl polymer has an average particle size of about 35 microns to about 60 microns. In an embodiment, greater than 99.0% of the particles of the pre-polymerized vinyl polymer have a particle size of greater than about 1.0 micron.

The pre-polymerized polymer is typically present in the bone cement composition at about 60.0% by weight to about 75.0% by weight of total weight of the first component. In a particular embodiment, the pre-polymerized polymer is present in the bone cement composition at about 65.5% by weight to about 70.5% by weight, such as about 67.5% to about 68.5% by weight of the total weight of the first component.

The first component of the bone cement composition further includes a radical donor. The radical donor is typically used to initiate a polymerization reaction with the reactive monomer present in the second component. In an embodiment, any known radical donor may be used. In an exemplary embodiment, the radical donor may be benzoyl peroxide (BPO), azo-bis-isobutyrylnitrile (AIBN), and mixtures thereof. In a particular embodiment, the radical donor is benzoyl peroxide (BPO). Typically, the radical donor is present at not greater than about 3.0% by weight of the total weight of the first component. In an embodiment, the radical donor is present at about 0.5% by weight to about 3.0% by weight, such as about 0.8% by weight to about 3.0% by weight, such as about 0.8% by weight to about 2.0% by weight, such as about 1.5% by weight to about 2.0% by weight of the total weight of the first component.

The first component of the bone cement composition further includes a contrast agent. The contrast agent may be selected depending on the medical instrumentation used to view the contrast agent. Suitable contrast agents include, for example, barium sulfate ($BaSO_4$), zirconium dioxide, $CHI_3$, $Na_2FPO_3$, and $CaF_2$. In an exemplary embodiment, the contrast agent is barium sulfate. Typically, the barium sulfate contrast agent may be imaged by fluoroscopy. In an embodiment, the barium sulfate is present at an amount sufficient to allow continuous imaging by fluoroscopy during the medical procedure, such as the injection of the bone cement in a patient, without impacting the mechanical properties or the desired setting time of the bone cement. The contrast agent is typically present at not less than about 20% by weight of the total weight of the first component. In an embodiment, the contrast agent is present at about 25% by weight to about 35% by weight, such as about 28% by weight to about 35% by weight, such as about 30% by weight to about 35% by weight, or even 30% by weight to about 32% by weight of the total weight of the first component.

In a particular embodiment, the contrast agent has an average particle size of about 0.3 microns to about 10.0 microns, such as about 0.3 microns to about 2 microns, such as about 2.0 microns. In an embodiment, the contrast agent has an average particle size of about 1.0 micron to about 5.0 microns. In an embodiment, greater than 99.0% of particles of the contrast agent have a size of less than about 10.0 microns. In an embodiment, when viewed under scanning electron microscopy (SEM), the particles of the contrast agent typically are spherical in shape and appear as amorphous agglomerates. In particular, the contrast agent as present in the first component typically appears as amorphous agglomerates distributed on the surface of the pre-polymerized vinyl polymer particles. In an embodiment, at least about 60%, such as at least about 70%, such as at least about 80% of the particles of the contrast agent are distributed on the surface of the pre-polymerized vinyl polymer particles. In other words, there are less than about 40%, such as less than about 30%, such as less than about 20% "freely floating" contrast agent particles that are not distributed on the surface of the pre-polymerized vinyl polymer.

The first component can further include optional ingredients. Optional ingredients include, for example, antibiotics, cytostatis agents, analgesic agents, disinfectants, preservatives, growth factors, proliferative factors, proteins, peptides, biopolymers, dyes, and mixtures thereof. In an exemplary embodiment, the optional ingredient includes gentamycine, tobramycine, clindamycine, vancomycine, β-TGF or an analog thereof, a bone morphogenic protein series compound, and mixtures thereof. Additionally, the bone cement composition is substantially free of hydroxyapatite. Further, the bone cement composition is substantially free of fluoride salt. "Substantially free" as used herein refers to a less than 99.99% by weight of the total composition.

The second component of the bone cement composition is generally referred to as a liquid component. The second component includes a reactive monomer, which reacts with the radical donor and polymerizes. In an embodiment, the reactive monomer is a methyl methacrylate (MMA), PEG monoacrylates, PEG diacrylates, PEG monomethylacrylates, PEG dimethyacrylates, PEG-mono/di-acrylates/methyacrylate, butanediol methacrylates, polyolefin-acrylates, urethaneacrylates, methacrylates, and mixtures thereof. Among the PEG-based reactive monomers, they typically have a molecular weight of about 200 Daltons (D) to about 1500 D. In an exemplary embodiment, the reactive monomer is methyl methacrylate (MMA).

The second component typically includes about 10.0% by weight to about 99.9% by weight of the reactive monomer, based on the total weight of the second component. In an embodiment, the reactive monomer is present at about 80% by weight to about 99.9% by weight, such as about 95.0% by weight to about 99.9% by weight, such as about 98.5% by weight to about 99.9% by weight of the total weight of the second component.

In an embodiment, the second component includes a polymerization accelerator. Typically, the polymerization accelerator is selected such that the polymerization reaction occurs at or below normal body temperatures so as not to cause thermal damage to the surgical site or surrounding areas. In an embodiment, the polymerization accelerator is a tertiary amine. In an exemplary embodiment, the tertiary amine includes, but is not limited to, dimethylparatoluidine (DMPT) and dihydroxyethylorthotoluidine.

In an embodiment, an advantageously low level of polymerization accelerator is used. Although DMPT is believed to be toxic to humans, the bone cement composition of the present disclosure contains particularly low levels without adverse consequences to the patient or the mechanical properties and setting time of the bone cement composition. For instance, the polymerization accelerator is present at less than about 1.0% by weight, such as even less than about 0.5% by weight of the total weight of the second component. In an embodiment, the polymerization accelerator is present at about 0.2% by weight to about 1.0% by weight, such as about 0.2% by weight to about 0.5% by weight of the total weight of the second component.

In an embodiment, the second component further includes a radical scavenger. Typically, the radical scavenger is present to retard or arrest the ability of the reactive monomer to self-polymerize. In an exemplary embodiment, the reactive monomer does not polymerize until the first component and the second component are mixed. In an embodiment, the radical scavenger is hydroquinone, hydroquinone monomethylether, vitamin E, and mixtures thereof. In an exemplary embodiment, the radical scavenger is hydroquinone monomethylether. The radical scavenger is typically present at an amount to prevent the reactive monomer from self-polymerizing. In an embodiment, the radical scavenger is present at an amount of about 30 ppm to about 400 ppm, such as about 50 ppm to about 200 ppm, or even about 20 ppm to about 100 ppm.

The second component may further include ingredients such as a diluent, a dye, an admixture of proteins, a chemotherapeutic, a drug, an antibiotic, and mixtures thereof. The admixture of proteins may include, for example, an admixture of heat sensitive/unsensitive proteins such as mitogenic growth factors, morphogenic growth factors, and mixtures thereof. An example of a suitable drug that can be included in the second component is bisphophonate.

In an embodiment, an optional diluent is added to the second component. Any suitable diluent may be used. Suitable diluents include, for example, polyethylene glycol (PEG), an ester of mellitic acid, and mixtures thereof. In an embodiment, the diluent is polyethylene glycol. An exemplary ester of mellitic acid is tri-octylmellitic ester. Generally, the diluent should have a molecular weight such that the diluent remains in liquid form at room temperature. For example, in an exemplary embodiment, the polyethylene glycol has a molecular weight of about 100 Daltons (D) to about 1000 D, such as about 400 D to about 800 D. When included, the diluent provides multiple benefits to the bone cement composition. For instance, the diluent desirably provides the ability to control the stiffness of the bone cement composition after curing/hardening. While not wishing to be bound by any particular theory, it is believed that lower stiffness is beneficial because it better simulates the actual properties of human bones. The presence of polyethylene glycol in the aforementioned weight range does not adversely affect the compressive strength and bending strength of the preparation. Thus, the stiffness can be more readily/easily controlled by the presence of polyethylene glycol, without compromising the compressive strength and the bending strength of the preparation relative to the previously known bone cement preparations. The compressive and bending strengths may be adversely affected when the amount of diluent exceeds 30% by weight, based on the total weight of the composition. In an embodiment, the diluent may be present at about 1% by weight to about 90% by weight, such as 5% by weight to about 60% by weight, such as about 10% by weight to about 40% by weight of the total weight of the second component. Furthermore, the presence of the diluent rapidly destabilizes the radical donor (thus, resulting in a faster hardening of the preparation) and reduces the amount of polymerization accelerator needed.

When a dye is present in the first or second component, it does not impart any mechanical attributes to the composition. Typically, the dye is used as an aid to assist the user (for instance, the surgeon, medical technician, aid, or nurse). In an embodiment, the dye can be used to readily inform the surgeon of the type of composition he or she is using. For instance, a purple-colored dye may have become known in the field by users to be indicative of a bone cement composition suitable for use in the spine, whereas a different color material may be known in the art by users to be indicative of a bone cement composition suitable for another application. In an embodiment, the dye is present at about 1% by weight to about 10% by weight of the total weight of the first component or second component.

The bone cement composition is typically prepared by a method that includes mixing the first and second components under conditions suitable to form the reaction product. In an embodiment, the reaction product is curable under standard pressure and at a temperature of about 18° C. to about 25° C., such as about 20° C. to about 25° C. In an embodiment, the weight ratio of the first component to the second component is about 2.2:1 to about 3.3:1, such as about 2.5:1. Further, the mixing may be done by any suitable mixing device.

When the first and second components are combined, a polymerization reaction is initiated by the polymerization accelerator present in the second component and the radical donor present in the first component. In practice, the radical donor will decompose when it encounters the polymerization accelerator evolving a free radical that will attack the double bonds present in the monomer causing the monomer to polymerize and ultimately, harden. The reaction in the context of the composition will yield a cured composition.

The bone cement component has desirable processing properties. In particular, once the bone cement composition is mixed, it has an average setting time of about 13 minutes. The setting time is the cumulative time it takes for the reaction product to form a cured product once mixing of the first and second component has been initiated. "Cure" as used herein refers to a viscosity of at least greater than about 2000 Pa-s. In an embodiment, the setting time is about 8 minutes to about 14 minutes, such as about 9 minutes to about 13 minutes, such as about 10 minutes to about 12 minutes. In an embodiment, the setting time of the bone cement composition is about 9 minutes. In an embodiment, the median setting time of the bone cement composition is about 11 minutes. In a particular embodiment, setting of the bone cement composition occurs at standard temperature (about 22° C.). In a further embodiment, the setting time of the composition is not greater than about 14 minutes. In certain medical applications, a shorter setting time is desired to decrease the surgeon's waiting time while the bone cement composition cures. Accordingly, a lower setting time is beneficial to the patient since it decreases the total time of the medical procedure.

Further, once mixing of the first component and the second component is initiated, the viscosity of the bone cement composition reaches a viscosity of about 200 Pascal-second (Pa-s) at a time of greater than about 2:30 minutes. In an embodiment, the viscosity of the bone cement composition reaches a viscosity of about 500 Pa-s at a time of greater than about 3:15 minutes (195 seconds). Typically, the bone cement composition reaches a viscosity of about 1000 Pa-s at a time of greater than about 4:00 minutes.

In an exemplary embodiment, the bone cement composition advantageously exhibits desirable mechanical properties when cured. For instance, the bone cement composition has advantageous compression strength when cured. In an embodiment, the compression strength of the bone cement composition after 6 days of storage and tested on a Zwick testing machine Z010, according to ASTM F451-99a and ISO 5833, is greater than about 75.0 MPa, such as greater than about 80.0 MPa, such as greater than about 100.0 MPa, such as even greater than about 105.0 MPa, providing a composition within medical strength regulations and guidelines usable for surgical implants.

In an exemplary embodiment, the components of the composition are capable of being readily injectable through a syringe-like device or other delivery mechanism to a surgical site, where they react to form the composition and cure to the hardened state. The composition is persistent at the surgical site, preferably adhering to the tissue and/or bone at the site. Furthermore, the composition is stable in that it generally does not undergo any significant changes in situ. When set/cured, the composition is also tough and elastic in that it is capable of bearing loads without experiencing undue or permanent deformation. Still further, the composition is believed to be well tolerated by the body in that it produces, at most, tolerable levels of immune and inflammatory responses. It is to be appreciated, however, that in exemplary embodiments of the compositions, while satisfying at least some of these advantages, may not satisfy all of these advantages in every instance.

In an embodiment, the composition is sold and distributed to users in a kit where the first and second components are maintained apart (e.g., separately packaged or contained) until they are ready for use in forming the composition. The user may receive a mixer apparatus containing the components in separate compartments thereof. See generally, U.S. Pat. Nos 6,241,734, 6,613,054, 7,018,089, and U.S. Patent application publication No. 2002/0191487 A1. These publications generally describe suitable apparatus for mixing and delivering the composition's components and mixtures thereof to form the composition. The components likely will be mixed by the user immediately prior to the surgical procedure with a suitable mixing apparatus. In an embodiment, the composition may be formed by mixing the first and second components and the composition is transferred to an apparatus suitable to deliver the composition (or mixture of the components) to the surgical site before the composition (or mixture) sets and cures.

The composition may be applied using a variety of mechanisms such as, for example, those described in U.S. Pat. Nos. 5,972,015 and 6,066,154. These patents generally describe a procedure referred to as "Kyphoplasty", which uses one or two balloons, similar to angioplasty balloons, to reduce the vertebrae bone fracture and restore vertebral height prior to injecting a bone cement composition. In an example, two balloons are introduced into the vertebra via bilateral transpedicular cannulae. The balloons are inflated to reduce the fracture, then deflated and removed, leaving a relatively empty cavity into which a bone cement composition is injected. The inflation of the balloons and subsequent injection of the composition helps restore vertebral height.

EXAMPLE 1

Seven formulations are prepared for a performance study. Specifically, the setting time of the formulations are measured for three varying amounts of polymerization accelerator. A first component (i.e. a dry or powder component) is prepared by combining (a) about 208.4 grams of polymethyl methacrylate polymer (PMMA) obtained from Roehm GmbH & Co. KG, Darmstadt, Germany, having a molecular weight of 200,000 g/mole to about 500,000 g/mole, (b) about 91.8 grams of barium sulfate obtained from Merck KGaA, Darmstadt, Germany, and (c) about 5.8 grams of benzoyl peroxide (BPO) obtained from Degussa Initiators GmbH, Pullach, Germany. These ingredients are mixed together in a ball mill rotating at a speed of about 200 rotations per minute with 405 grams of Stealit balls of 20.0 mm diameter for 50 minutes. A second component (i.e. the wet component) is prepared and includes (a) about 8.97 grams of methyl methacrylate (MMA) obtained from Roehm GmbH & Co. KG, Darmstadt, Germany, (b) about 0.027 grams to about 0.045 grams of N,N-dimethyl-p-toluidine (DMPT) obtained from Roehm GmbH & Co. KG, Darmstadt, Germany, (c) about 50 parts per million (ppm) of hydroquinone monomethylether obtained from Merck KGaA, Darmstadt, Germany. The first component (20.0 grams) and the second components (9.0 grams) are mixed together at standard temperature and pressure and are set to provide a hardened material. The handling characteristics are measured at standard temperature (about 22° C.). Setting time measurements are conducted according to ASTM F451-99a and ISO 5833-92. Setting characteristics is illustrated in Table 1.

TABLE 1

| | DMPT g/% (by weight of second component) | Temperature (° C.) | Setting Time (minute) |
|---|---|---|---|
| Formulation 1 | 0.045 g/0.5% | 19.7 to 19.9 | 11:08 |
| Formulation 2 | 0.027 g/0.3% | 24.8 to 24.9 | 8:40 |
| Formulation 3 | 0.027 g/0.3% | 23.9 | 8:40 |
| Formulation 4 | 0.027 g/0.3% | 24.5 | 8:25 |
| Formulation 5 | 0.0315 g/0.35% | 20.6 | 13:55 |
| Formulation 6 | 0.027 g/0.3% | 20.6 | 13:50 |
| Formulation 7 | 0.0315 g/0.35% | 20.4 to 20.6 | 13:30 |
| Formulation 8 | 0.0315 g/0.35% | 20.3 to 20.7 | 12:22 |
| Formulation 9 | 0.0315 g/0.35% | 19.8 to 20.5 | 13:45 |

The nine formulations have setting times ranging from 8:25 minutes to 13:55 minutes. Results in Table 1 further demonstrate that the level of DMPT used in the bone cement composition can be advantageously low and less toxic to the patient and still have an advantageously low setting time.

The average setting time is measured for Formulation 2 using a single factor ANOVA analysis at an average ambient temperature of about 22.7° C. Four runs are conducted and the data is seen in Table 2.

TABLE 2

| Run | Ambient Temperature (° C.) | Setting Time (minute) |
|---|---|---|
| 1 | 22.6 | 13.4 |
| 2 | 22.9 | 12.9 |
| 3 | 22.9 | 12.9 |
| 4 | 22.5 | 13.0 |
| Average (Std. Dev.) | 22.7 (0.2) | 13.1 (0.3) |
| Range | 22.5-22.9 | 12.9-13.4 |

As seen in Table 2, the average setting time is about 13 minutes at ambient temperature.

EXAMPLE 2

The mechanical properties of the several formulations are evaluated. The method for preparing the formulation and components of the formulation used are described in Example 1. There are variations in the amount of benzoyl peroxide (BPO), N, N-dimethyl-p-toluidine (DMPT), and hydroquinone monomethylether (HQME). The test slabs are compression molded at 23+/−1° C. for one hour and post-cured at 23+/−1° C. for 6 days. Compression strength measurements are carried out according to ASTM F451-99a and ISO 5833 on a Zwick testing machine Z010. The results are summarized in Table 3.

TABLE 3

| BPO (% w/w) | DMPT (% w/w) | HQME (ppm) | Compression strength (MPa) |
|---|---|---|---|
| 1.92 | 0.2 | 50 | 75.52 +/− 1.75 |
| 1.92 | 0.3 | 50 | 94.33 +/− 2.86 |
| 1.92 | 0.5 | 50 | 104.26 +/− 1.53 |
| 1.92 | 0.7 | 50 | 106.21 +/− 1.18 |
| 1.92 | 1.0 | 50 | 108.46 +/− 3.86 |
| 1.92 | 0.3 | 20 | 82.90 +/− 2.17 |
| 1.92 | 0.3 | 50 | 94.33 +/− 2.86 |
| 1.92 | 0.3 | 100 | 88.18 +/− 3.17 |
| 0.80 | 0.3 | 50 | 80.15 +/− 2.44 |
| 0.98 | 0.3 | 50 | 96.07 +/− 1.63 |
| 1.92 | 0.3 | 50 | 94.33 +/− 2.86 |
| 2.83 | 0.3 | 50 | 88.80 +/− 4.09 |
| 3.00 | 0.3 | 50 | 87.66 +/− 1.00 |

As seen in Table 3, a decrease in the level of DMPT does not have an adverse impact on the mechanical properties of the bone cement. Advantageously low levels of DMPT as well as BPO and HQME provide bone cement compositions that have desirable compression strength for medical applications.

EXAMPLE 3

Viscosity of a bone cement formulation is measured. The viscosity prior to setting of the bone cement is evaluated. The method for preparing the formulation and components of the formulation used are described in Example 1. DMPT is present at about 0.3% by weight and HMQE at 50 ppm. Viscosity measurements are performed on a rotating shear rheometer. The parameters are as follows: TA Instruments AR 1000 Controlled Stress Rheometer having a 4 cm stainless steel parallel plate. Gap: 1000 μm; Temperature: 23° C.; Shear rate: 0.5 s$^{-1}$; Sampling rate: 0.5 Hz.

The cements are hand mixed in air and loaded into the rheometer. After the sample is loaded, the excess cement is wiped away, leaving a uniform edge at the upper geometry. A timer is started at the onset of mixing and the rheology test start time is recorded. Shearing characterization begins at less than three minutes after the start of mixing. All data is reported as time from the start of mixing. Data collection stops when the viscosity reaches 1000 Pa-s to allow the cement to be removed from the rheometer before it completely hardens.

Results can be seen in FIG. 1. The viscosity of the bone cement formulation is measured in triplicate and follows the same trend with good reproducibility. The deviation from a linear trend, as seen in FIG. 1 is the result of slippage as the edges of the cement exposed to the atmosphere cure faster than the cement at the center of the plate. The viscosity of the bone cement composition reaches a viscosity of about 200 Pascal-second (Pa-s) at a time of greater than about 2:30 minutes (150 seconds). In an embodiment, the viscosity of the bone cement composition reaches a viscosity of about 500 Pa-s at a time of greater than about 3:15 (195 seconds) minutes. Typically, the bone cement composition reaches a viscosity of about 1000 Pa-s at a time of greater than about 4:00 minutes.

The above-disclosed subject matter is to be considered illustrative, and not restrictive, and the appended claims are intended to cover all such modifications, enhancements, and other embodiments, which fall within the true scope of the present invention. Thus, to the maximum extent allowed by law, the scope of the present invention is to be determined by the broadest permissible interpretation of the following claims and their equivalents, and shall not be restricted or limited by the foregoing detailed description.

What is claimed is:

1. A composition comprising:
 a) a first component consisting essentially of a poly(methyl methacrylate) (PMMA) having a molecular weight of about 200,000 grams/mole to about 500,000 grams/mole, a contrast agent, and a radical donor; and
 b) a second component comprising methyl methacrylate (MMA), a radical scavenger, and a polymerization accelerator;
 wherein the composition reaches a viscosity of about 500 Pascal-second at a time of greater than about 3:15 minutes after mixing the first component and the second component and has an average setting time of about 13 minutes.

2. The composition of claim 1, wherein the composition is substantially free of hydroxyapatite.

3. The composition of claim 1, wherein the PMMA has an average particle size of about 35 microns to about 60 microns.

4. The composition of claim 1, wherein the contrast agent is present at not less than about 20% by weight of the total weight of the first component.

5. The composition of claim 4, wherein the contrast agent is present at about 30% by weight to about 35% by weight of the total weight of the first component.

6. The composition of claim 1, wherein the contrast agent is selected from the group consisting of barium sulfate ($BaSO_4$), zirconium dioxide, $CHI_3$, $Na_2FPO_3$, and $CaF_2$, and mixtures thereof.

7. The composition of claim 6, wherein the contrast agent has an average particle size of about 0.3 microns to about 10 microns.

8. The composition of claim 7, wherein the contrast agent has an average particle size of about 0.3 microns to about 2.0 microns.

9. The composition of claim 1, wherein the radical donor is selected from the group consisting of benzoyl peroxide (BPO), azo-bis-isobutyrylnitrile (AIBN), and mixtures thereof.

10. The composition of claim 9, wherein the radical donor is present at about 1.5% by weight to about 2.0% by weight of the total weight of the second component.

11. The composition of claim 1, wherein the radical scavenger is selected from the group consisting of hydroquinone monomethylether, hydroquinone, vitamin E, and mixtures thereof.

12. The composition of claim 1, wherein the polymerization accelerator is selected from the group consisting of dimethylparatoluidine (DMPT), dihydroxyethylorthotoluidine, and mixtures thereof.

13. The composition of claim 12, wherein the polymerization accelerator is present at about 0.2% by weight to about 1.0% by weight of the total weight of the second component.

14. The composition of claim 13, wherein the polymerization accelerator is present at about 0.2% by weight to about 0.5% by weight of the total weight of the second component.

15. The composition of claim 1, wherein the composition has a setting time of about 9 minutes.

16. The composition of claim 1, further comprising an optional ingredient selected from the group consisting of an antibiotic, a cytostatic agent, an analgesic agent, a disinfectant, a preservative, a growth factor, a proliferative factor, a protein, a peptide, a biopolymer, a dye, a chemotherapeutic, a drug, and mixtures thereof.

* * * * *